(12) United States Patent
Barnes et al.

(10) Patent No.: US 7,798,710 B1
(45) Date of Patent: Sep. 21, 2010

(54) MOBILE RADIOGRAPHY SYSTEM AND GRID ALIGNMENT

(76) Inventors: Gary T. Barnes, 2250 Shady Creek Trail, Birmingham, AL (US) 35216; David M. Gauntt, 403 Poinciana Dr., Homewood, AL (US) 35209

( * ) Notice: Subject to any disclaimer, the term of this patent is extended or adjusted under 35 U.S.C. 154(b) by 0 days.

(21) Appl. No.: 12/550,734

(22) Filed: Aug. 31, 2009

Related U.S. Application Data

(63) Continuation of application No. 11/349,424, filed on Feb. 7, 2006, now Pat. No. 7,581,884.

(51) Int. Cl.
*A61B 6/08* (2006.01)
(52) U.S. Cl. ............... 378/206; 378/154; 378/197; 378/198
(58) Field of Classification Search .......... 378/154, 378/197, 198, 206
See application file for complete search history.

(56) References Cited

U.S. PATENT DOCUMENTS

| | | | | |
|---|---|---|---|---|
| 4,092,544 | A * | 5/1978 | Grim | ............... 378/206 |
| 4,752,948 | A | 6/1988 | MacMahon | |
| 4,885,761 | A | 12/1989 | Sones | |
| 5,241,578 | A | 8/1993 | MacMahon | |
| 5,388,143 | A | 2/1995 | MacMahno | |
| 5,499,284 | A | 3/1996 | Pellegrino | |
| 6,155,713 | A | 12/2000 | Watannabe | |
| 6,447,164 | B1 * | 9/2002 | Polkus | ............... 378/206 |
| 6,491,429 | B1 | 12/2002 | Suhm | |
| 6,702,459 | B2 | 3/2004 | Barnes | |
| 6,851,851 | B2 * | 2/2005 | Smith et al. | ............... 378/189 |
| 7,014,362 | B2 * | 3/2006 | Beimier et al. | ............... 378/206 |
| 7,581,884 | B1 * | 9/2009 | Barnes et al. | ............... 378/205 |

OTHER PUBLICATIONS

Niklason, LT, Sorenson, JA, Nelson, JA; Scattered Radiation in Chest Radiology; Med. Phys. 8:677-681, 1981.
Niklason, LT, Barnes, GT, Carson, P; Accurate Alignment Device for Protable Radiography; Radiology 173 (P):452, 1989.
Barnes, GT; Contrast and Scatter in X-ray imaging; Radiographics; 11:307-232, 1991.
O'Donovan, PB, Skipper, GJ, Litchney, JC, Salupo, AJ, Bortnick, JR; Device for Facilitating Precise Alignment in Bedside Radiography; Radiology 184: 284-285, 1992.
Tucker, DM, Souto, Barnes, GT; Scatter in Computer Radiology; Radiology; 188:271-274, 1993.

* cited by examiner

*Primary Examiner*—Edward J Glick
*Assistant Examiner*—Thomas R Artman
(74) *Attorney, Agent, or Firm*—Bradley Arant Boult Cummings, LLP

(57) ABSTRACT

Disclosed is a mobile radiographic unit with improved x-ray scatter control. Improved x-ray scatter control is provided through the alignment of the system with the focal line of an anti-scatter grid. In a preferred embodiment, the system comprises an x-ray source assembly, a tube housing mounting, a measuring system, a motion control system and a processor in communication with the measuring system and the motion control system.

24 Claims, 13 Drawing Sheets

MOBILE RADIOGRAPHY SYSTEM AND GRID ALIGNMENT

CROSS REFERENCE TO RELATED APPLICATIONS

The present disclosure is a continuation of U.S. patent application Ser. No. 11/349,424, filed 2-7-2006, now U.S. Pat. No. 7,581,884, issued Sep. 1, 2009.

FIELD OF THE INVENTION

The present disclosure relates to radiography and particularly to mobile radiography.

BACKGROUND

In the hospital setting, mobile radiographic exams are performed on patients that are incapable of being moved, or are difficult to move. In tertiary care medical centers, mobile radiographic exams represent a significant percentage of the radiographic exams performed. X-rays passing through an object, such as a human body, experience some degree of scatter associated with interactions of the x-rays with atoms or electrons. The primary x-rays transmitted through an object travel on a straight line path from the x-ray source (also referred to herein as the x-ray focal spot) to the image receptor and carry object density information. Scattered x-rays form a diffuse image that degrades primary x-ray image contrast. In thick patients, scattered x-ray intensity exceeds the intensity of primary x-rays. Scattering phenomena is well known and routinely compensated for in general radiography, fluoroscopy and mammography through the use of anti-scatter grids.

An anti-scatter grid includes a laminate of lead foil strips interspersed with strips of radiolucent material (FIG. 1). The grid is positioned between the object to be imaged and the image receptor and oriented such that the image forming primary x-rays are incident only with the edges of the lead foil strips. Thus, the majority of primary x-rays pass through the radiolucent spacer strips. In contrast, scattered x-rays are emitted in all directions due to interaction with the object and as such, scattered x-rays are incident on a larger area of the lead strips and only a small percentage of scattered x-rays reach the image receptor, as compared to primary x-rays. The degree of scatter control for a given grid depends upon the grid ratio, which is defined as the ratio of the radiopaque strip thickness in the direction of the x-ray path to the width of the radiolucent spacer material as measured orthogonal to the x-ray beam path. Thus, the higher the grid ratio, the greater the scatter control. A high grid ratio, while more effective in reducing scattered x-rays, is also more difficult to align relative to the x-ray focal spot. In order to compensate for x-ray beam divergence in a focused grid, the radiopaque strips are tilted to a greater extent with increasing distance from the center of the grid. The planes of the grid vanes all converge along a line known as the focal line. The distance from the focal line to the surface of the grid is referred to as the focal length of the grid. The focal line coincides with the straight line path to the focal spot (illustrated in FIG. 2). Thus, when the focal spot is coincident with the focal line of the grid, the primary x-rays have minimal interaction with the radiopaque lead strips and maximal primary transmission is obtained. Misalignment of the focal line of the anti-scatter grid with the focal spot diminishes primary x-ray transmission while scattered x-ray transmission remains unchanged. Thus, optimal primary x-ray transmission requires alignment (positional and orientation) of the focal spot with the focal line of the anti-scatter grid.

In general radiography, fluoroscopy and mammography, the image receptor and x-ray tube housing (comprising the x-ray source) are rigidly mounted and in a fixed position relative to one another, thereby making focal spot and grid alignment a simple process. In mobile radiography, an image receptor is placed under a bedridden patient and the x-ray source, mounted at the end of a jointed arm, is positioned above the patient. Since the relative separation of the focal spot and the image receptor is variable, determining the proper position and orientation of an anti-scatter grid between a patient and the image receptor becomes a difficult alignment problem. If a grid is not used, only a small fraction of the possible contrast is obtained in the x-ray image. As a result, scatter to primary x-ray ratios of 10:1 or more are common in chest and abdominal bedside radiography resulting in less than 10% of the possible image contrast being obtained in mobile radiographic films (1,2). Contrast limitations are exacerbated if digital storage phosphor image receptors are utilized in place of the more conventional screen-film systems (3).

When grids are utilized in conjunction with mobile radiography, the grid is typically not aligned. Misalignment problems are diminished by utilizing a grid having a low ratio of 8:1 or less. Although x-ray image contrast is improved with the use of a low ratio grid as compared to current clinical practice, the contrast remains significantly lower than otherwise could be obtained with a properly aligned, high ratio grid having a grid ratio of 10:1 or greater.

Thus while mobile radiography is in many ways more convenient than fixed installation radiography, its clinical utility is diminished due to the inferior image quality caused by scattered radiation which is a greater problem in mobile radiography due to the difficulty in producing the proper alignment of the focal spot with the anti-scatter grids. A means to produce proper alignment that is easy for the operator to use would significantly improve mobile radiographic image contrast and image quality, and thus increase the clinical utility of mobile radiography.

The prior art has contains a number of mobile radiography systems; however, these system have been limited in their utility in clinical acceptability owing to the considerable additional effort required on the part of a radiography technologist to align the x-ray source or the cost and complexity of the systems described. Furthermore, these prior art system are too costly/complex to manufacture to be placed in routine operation. Therefore, there exists a need for a mobile radiography system having a simple, cost effective method to place the focal spot and the central x-ray beam in correct alignment (position and orientation) with regard to the anti-scatter grid. The present disclosure provides such a mobile radiography system and method for use therewith.

DETAILED DESCRIPTION

Figure 1:
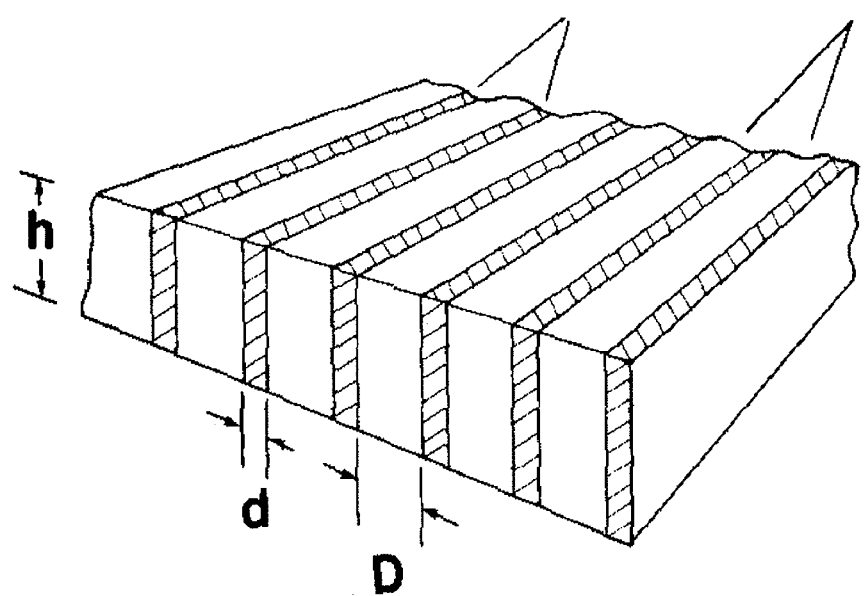
FIG. 1 is a schematic view of an anti-scatter grid common in the field.
Figure 2:
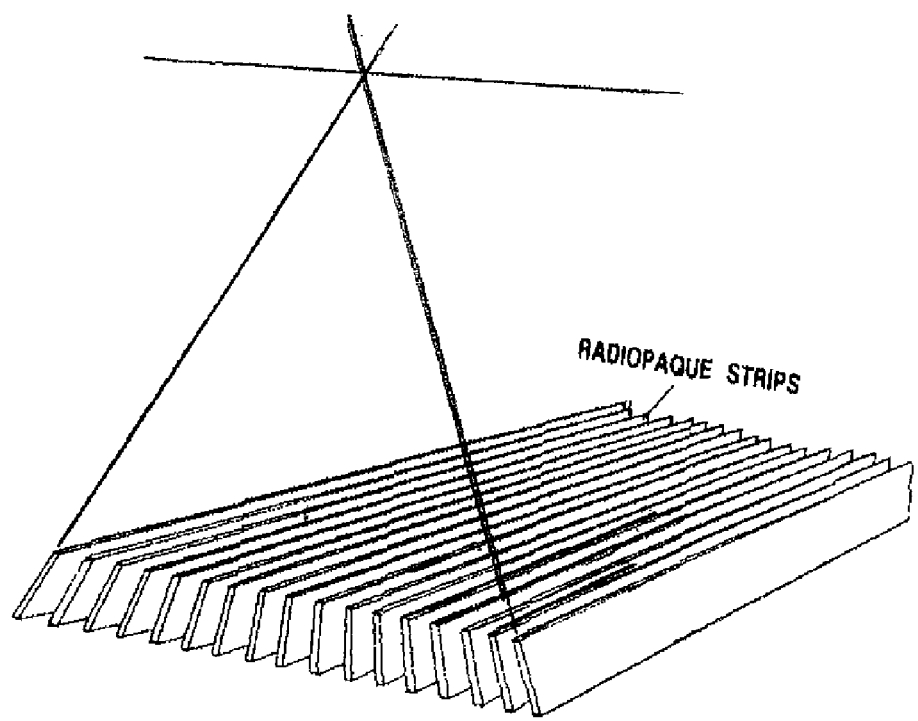
FIG. 2 is a schematic view of a focused anti-scatter grid common in the field.

The present disclosure provides a device and method to increase x-ray scatter control of mobile radiography equipment through optimal alignment of a focal spot with the focal line of an anti-scatter grid. A mobile radiography device and method according to the present disclosure affords a rapid and accurate alignment between a mobile radiographic device focal spot and the focal line of the anti-scatter grid. In one embodiment, the present disclosure describes a system generally comprising an x-ray source assembly, a measuring system, a motion control system and a processor to receive data from and transmit information to at least one of the measuring system and the motion control system. The measuring system utilizes a series of positional encoders for at least one degree of freedom in the mobile radiographic system, and a detecting element attached to a mobile radiographic system to provide position and orientation information of the anti-scatter grid relative to the radiographic system. The detecting element may be a single component, or a plurality of components. In one embodiment, the detecting element comprises a target array or other external object in a fixed position and orientation relative to the anti-scatter grid and a detector, such as a camera to provide such position and orientation information. A positional encoder is associated with at least one degree of freedom of the x-ray source assembly; the position and orientation of the x-ray source assembly can be determined from values of these encoders. The detecting element and positional encoders transmits this information to the processor which determines the position of the anti-scatter grid relative to a fixed point on the mobile radiography system. The processor determines the alignment of the focal spot and central x-ray beam relative to the anti-scatter grid for production of an optimal image. A motion control system allows alignment of the mobile radiographic system to position the x-ray focal spot to a state of alignment relative to the focal line of an anti-scatter grid. The motion control system utilizes a directing element in communication with said processor to aid in this process. The directing element guides the operator in adjusting the degrees of freedom of the mobile radiography system to position the x-ray focal spot to a state of alignment relative to the focal line of an anti-scatter grid. In one embodiment, the directing element is visual in nature, such as a visual display; in an alternate embodiment, the directing element is tactile in nature, such as a tactile display; in yet another embodiment, the directing element is auditory in nature, such as an auditory response. Regardless of the form of the directing element, the directing element informs the operator when at least one degree of freedom of the mobile radiography system has a desired value and provides information necessary to move the system into a state of alignment. The directing element may inform the operator of the current position of at least one degree of freedom of the mobile radiography system and the desired position of at least one degree of freedom of the mobile radiography system, or it may inform the operator of the direction in which at least one degree of freedom must be changed to move such degree of freedom to its desired value. In one embodiment, the directing element displays this information in real time. The directing element may also provide the operator with information regarding the status of the mobile radiographic system.

It is to be appreciated that the position and orientation of any rigid body can be described by six parameters. In some parameterizations, three parameters describe the position of a fiducial point in the rigid body, and the remaining three parameters describe the rotation of the body about this fiducial point. The position may be described in terms of Cartesian coordinates, spherical coordinates, cylindrical coordinates, or some other coordinate system. The rotation may be described in terms of an unit eigenvector of rotation and a rotation angle, by roll, pitch, and yaw angles, or some other coordinate system. Such parameterizations are made in relation to a specified frame of reference, and techniques to convert from one frame of reference to another are well known to those skilled in the art. In this specification, the term "Cartesian coordinates" will be used to describe parameterizations useful in converting from one frame of reference to another. Alternately, the position and orientation may be described by six parameters that determine position and orientation together rather than independently. An example of this is the six parameters H, R, $\Theta$, $\Omega$, $\Psi$, and $\Phi$ shown in FIG. 13. Such parameterizations are useful for describing the position and orientation of an object on a jointed arm, such as that illustrated in FIG. 13. In this specification, the term "degree of freedom" shall mean the motion of a single rotational or sliding joint in the arm holding the x-ray source assembly, or for the motion of a combination of joints constrained such that any point on the x-ray source assembly follows a path in space. In this specification, the term "value of the degree of freedom" shall mean a parameter describing the state of a single degree of freedom.

In the embodiment illustrated, the motion control system is manually driven by the technician/operator. In one embodiment, a high ratio anti-scatter grid is employed; however, any anti-scatter grid known in the art may be used. For the purpose of this specification, a high ratio anti-scatter grid is defined as a grid having a grid ratio of 10:1 or greater. Through the device and method of the present disclosure, the process of positioning the components of a mobile radiographic system to a state of alignment can be achieved with minimal operator involvement. Furthermore, the system can be produced at low cost with minimal complexity.

Figure 3:
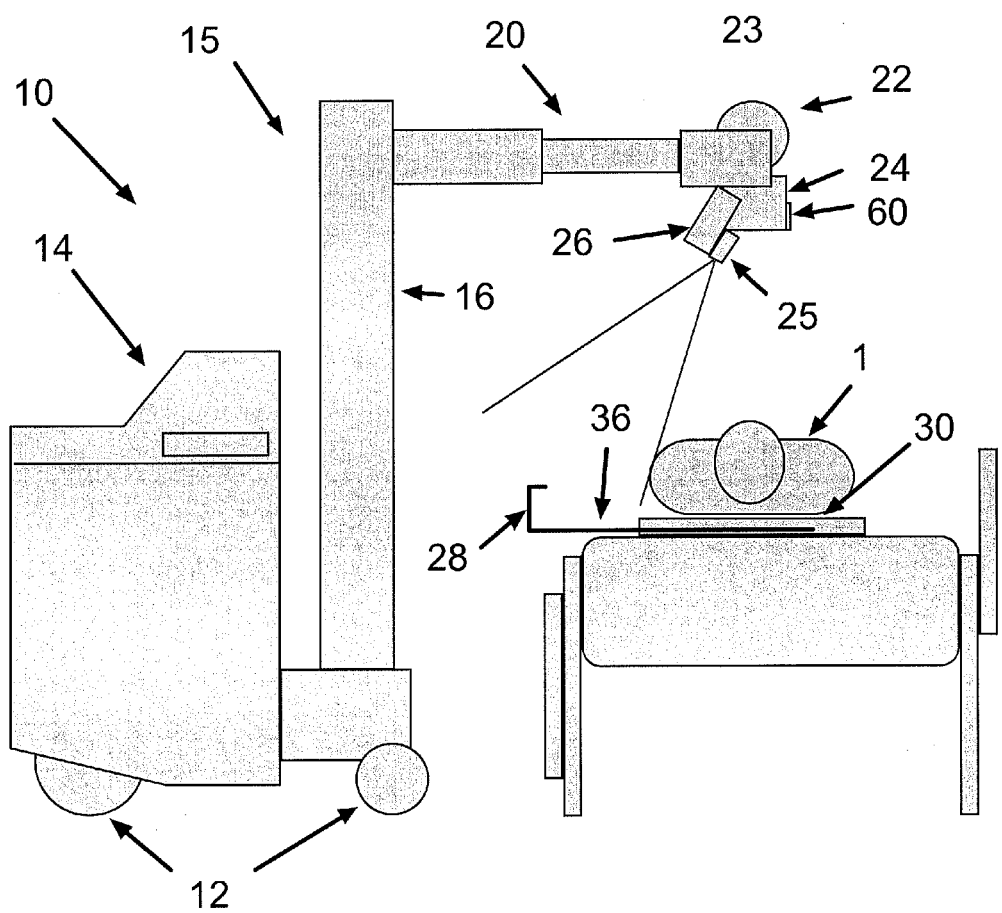
FIG. 3 is a side view of one embodiment of a mobile radiography system according to the present disclosure.
Figure 13:
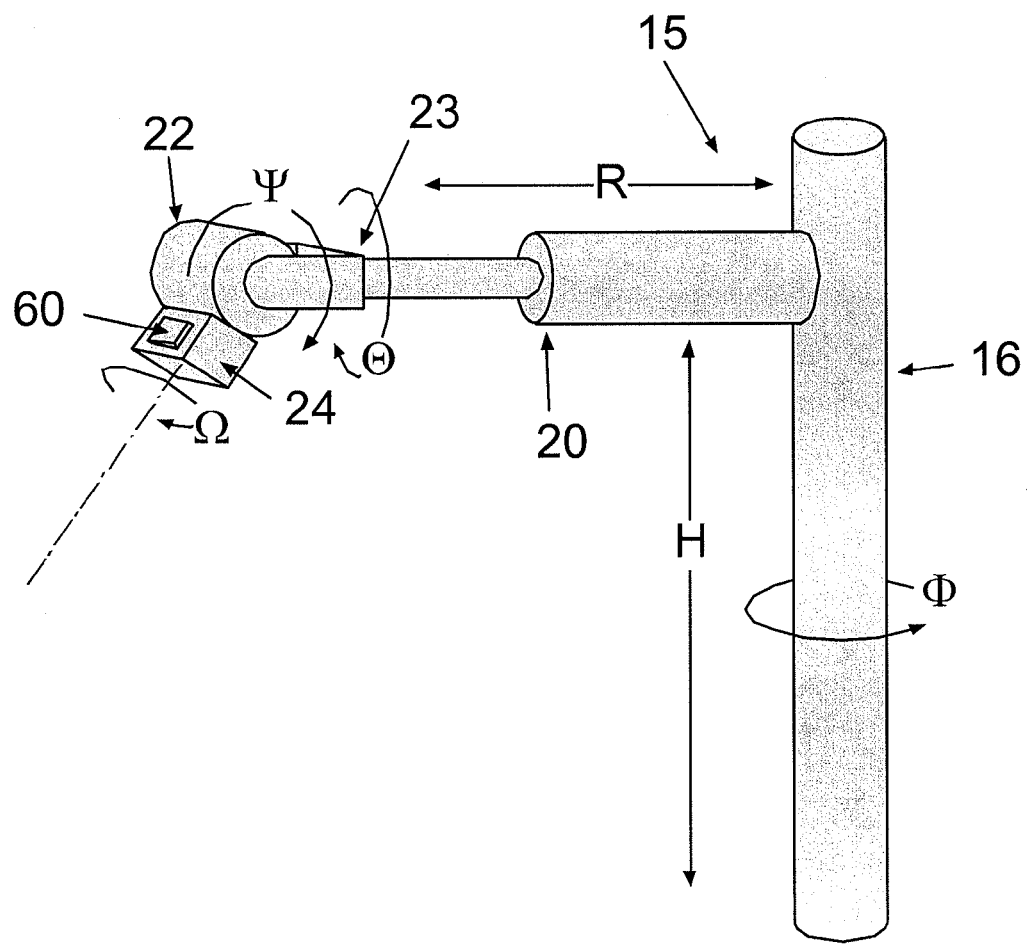
FIG. 13 illustrates one embodiment of the x-ray source assembly showing the different degrees of freedom in each component.

Referring now to FIG. 3, a particular embodiment of the mobile radiographic system 10 is described and includes a movable base 12, an operator's console 14, an x-ray source assembly and a tube housing mounting. The x-ray source assembly preferably has at least one degree of freedom and comprises an x-ray tube housing 22 containing an x-ray source, the tube housing 22 having an x-ray emission aperture (not shown), and a collimator 24 attached to the tube housing 22. The tube housing mounting has at least one degree of freedom to allow the x-ray source assembly to be positioned at a desired position and orientation (FIG. 13). In one embodiment, the tube house mounting comprises an adjustable, vertical column 16, an adjustable, horizontal arm 20 mounted to the column 16 and an adjustable gimbal 23 for coupling the x-ray tube housing 22 to the arm 20. The foregoing is illustrative of an x-ray mobile radiographic system known in the art; variations to the foregoing known to those of ordinary skill in the art are meant to be included in the scope of the present disclosure.

The mobile system 10 further comprises a processor and a measuring system. In this embodiment, the detecting element of the measuring system comprises a detector 26 (described in the presented embodiment as an optical detector, or camera) and a target array 28 in a fixed position and orientation relative to the anti-scatter grid; as discussed above the measuring system also comprises at least one position encoder. Each of the detector and positional encoder are in communication with the processor. Furthermore, a light source 25 may also be incorporated on the mobile radiographic system 10 as described herein.

Figure 6A:
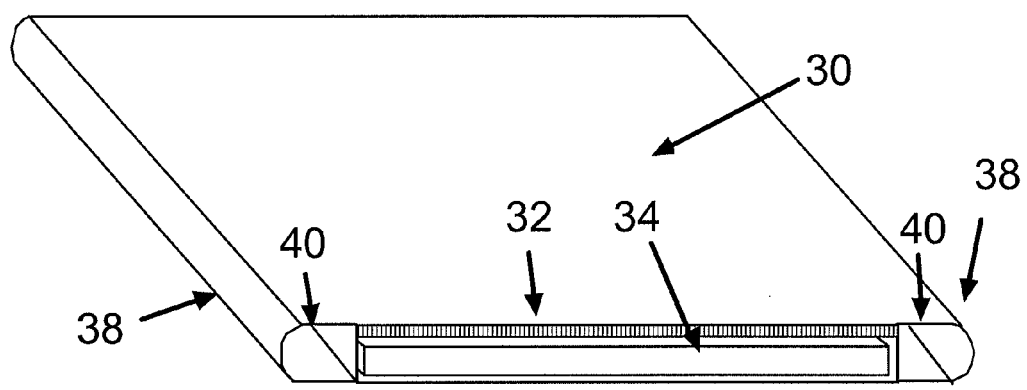
FIGS. 6A and 6B are perspective views of one embodiment of a grid tunnel of the present disclosure.

In one embodiment, the target array 28 is placed in a fixed position and orientation relative to the anti-scatter grid 32 through a target arm 36 removably coupled to the grid tunnel 30. The grid tunnel 30 contains the anti-scatter grid 32 and the image receptor 34. In one embodiment, the grid tunnel 30 comprises a channel to receive the target arm 36 (referred to as a channel 40) (FIGS. 6A and B). The target array 28 comprises a plurality of fiducial markers 50. In one embodiment, the detector 26 is attached to the mobile radiographic system 10. The placement of the detector 26 may be varied as desired.

Figure 6B:
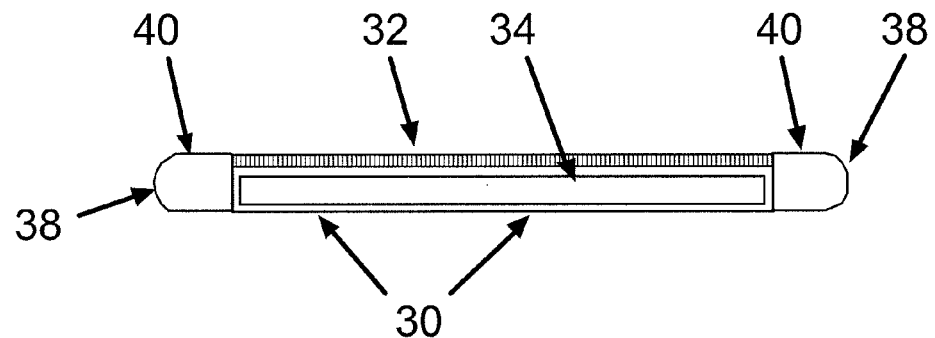

The detector 26 is positioned to acquire information, such as but not limited to an image, regarding the position and orientation of the target array 28 and its fiducial markers 50. In one embodiment, the information is an image; throughout the remainder of the specification, the information will be referred to as an image. The image is transmitted to the processor and the processor determines the position and orientation information of the grid tunnel 30 and therefore the anti-scatter grid 32, relative to the radiographic system via the fiducial markers 50 on the target array 28. An object to be radiographically imaged 1, such as a patient, is interspaced between the collimator 24 and the grid tunnel 30. The image receptor 34 is placed proximal to anti-scatter grid 32 and distal from an object, such as a patient 1 as is known in the art (FIGS. 3 and 6A and 6B).

Other means may be employed to determine the position and orientation of the anti-scatter grid relative to the mobile radiographic unit. In such alternate embodiment, the detector may be an ultrasound detector and the target array may comprise at least one ultrasound emitting element. Furthermore, the detector may be a magnetic dipole detector and the target array may comprise at least one magnetic element. In such embodiment, the target array may be supported by a target arm or may be affixed to the grid tunnel 30 or the anti-scatter grid 32. In yet a further embodiment, a mechanical linkage arm equipped with rotational and positional encoders, or combinations of accelerometers and gyroscopes mounted on the grid tunnel may be used. The use of accelerometers and gyroscopes, known as inertial navigation, measures the motion of the grid tunnel as it is moved from a dock fixedly mounted to the console 14 to its final position under the patient 1.

The following describes a specific embodiment of the grid tunnel 30, the target array 28 and the target arm 36. The following is exemplary in nature only and is not meant to restrict the present disclosure to the embodiments shown and described. The grid tunnel 30 and the target arm 36 are shown with greater clarity in FIGS. 5 and 6. The grid tunnel 30 is manufactured from material selected from the group including, but not limited to, rigid sheet metal, carbon fiber composites and impact resistant plastics, such as LEXAN (GE), polycarbonate, ABS and the like, or a combination of any of the above. In one embodiment, the grid tunnel 30 is manufactured from carbon fiber composites. The grid tunnel 30 has sufficient strength to support the patient 1, and is typically designed to support more than 200 kilos. The grid tunnel 30 may have rounded edge surfaces 38 to facilitate insertion under the patient 1. The arm 36 supports the target array 28, and may be constructed of the same materials as the grid tunnel 30. The arm 36 is adapted to insert within a channel 40 within the grid tunnel 30. A channel 40 may be provided along adjacent edges of the grid tunnel 30 to accommodate transverse (parallel to the short axis of the grid tunnel 30) and longitudinal (parallel to the long axis of the grid tunnel 30) orientations of the grid tunnel under the patient 1. Therefore, the target array 28 is placed in a fixed position and orientation relative to the anti-scatter grid 32; however, as it apparent from the foregoing, the target array may be removed from the grid tunnel 30 and may be positioned at one of several fixed orientations relative to the anti-scatter grid 32. The term fixed position and orientation should not imply the target array 28 is permanently coupled to the grid tunnel 30 or is permanently in only one fixed orientation with regard to the anti-scatter grid 32. Optionally, a hand grip may be included in the grid tunnel 30 to facilitate crude alignment of the grid tunnel 30 beneath patient 1. In one embodiment, the target array 28 extends a distance from the grid tunnel 30 to ensure visibility when a large patient 1 covers the grid tunnel 30.

Figure 5:
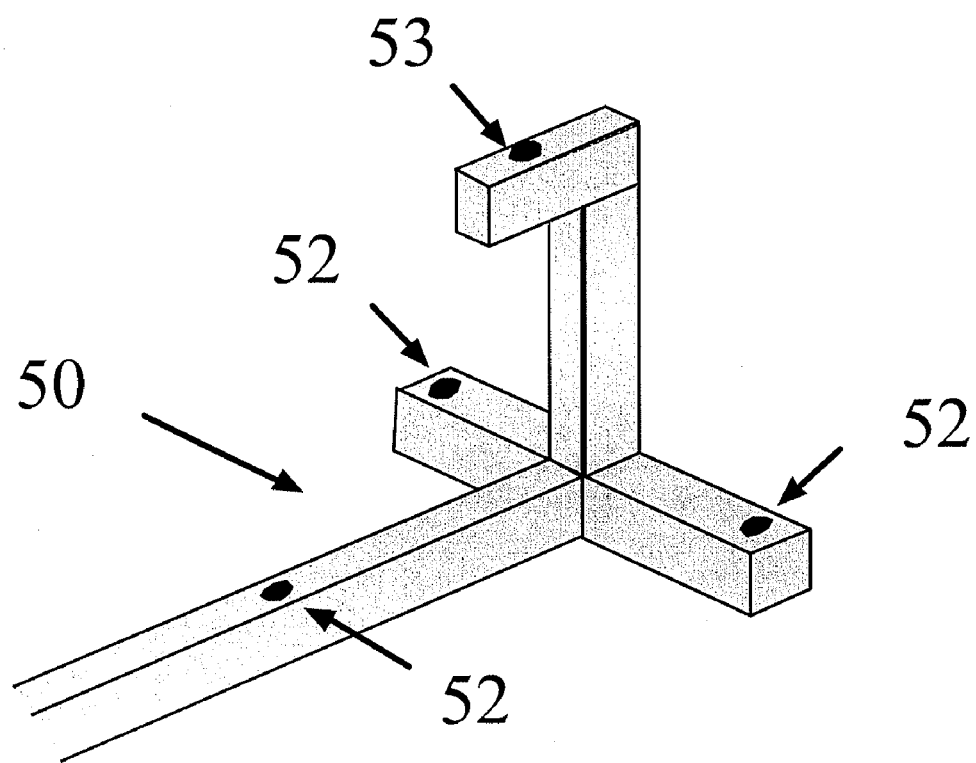
FIG. 5 is a perspective detail view of one embodiment of a target arm and fiducial markers according to the present disclosure.

FIG. 5 shows one embodiment of a target array 28 according to the present disclosure having a plurality of fiducial markers 50, the position of the fiducial markers 50 being fixed relative to the anti-scatter grid 32. In the embodiment illustrated in FIG. 5, three fiducial markers 52 are provided in a plane having a known position and orientation relative to the plane of the anti-scatter grid 32 to provide a measure of the distance from the target array 28 to the detector (illustrated as camera 26), and therefore, the x-ray tube housing 22. A fourth fiducial marker 53 is placed out of plane relative to the markers 52 provides a measure of transverse misalignment. The fiducial markers 50 may comprise a variety of materials. In one embodiment, the fiducial markers 50 are a light reflecting substance. In a specific embodiment, the light reflecting substance is a retro-reflecting material that transmits the reflected light in the direction in which the light impacted the material. In an alternate embodiment, the light reflecting substance is a corner mirror. The detector acquires an image of the target array 28 with a light source shining on the target array 28 (the light source 25 may be mounted on the detector 26 or other components of the mobile radiographic system 10) and acquires a second image with no light source shining on the target array 28. The processor subtracts the second image from the first image to produce an image that consists essentially of the light reflected back by the light reflecting material comprising the fiducial markers 50. This process increases the contrast between the fiducial markers and the background substantially. In an alternate embodiment, LEDs may be used as the fiducial markers. The use of LEDs as the fiducial marker is described in U.S. Pat. No. 6,702,459. The use of the light reflecting materials allows the use of a passive target arm 36 (without internal electronics and the ability to communicate with the processor) and greatly simplifies the construction of the target arm 36 and avoids any requirement of communication between the target array 28, the target arm 36 and the processor.

Figure 4:
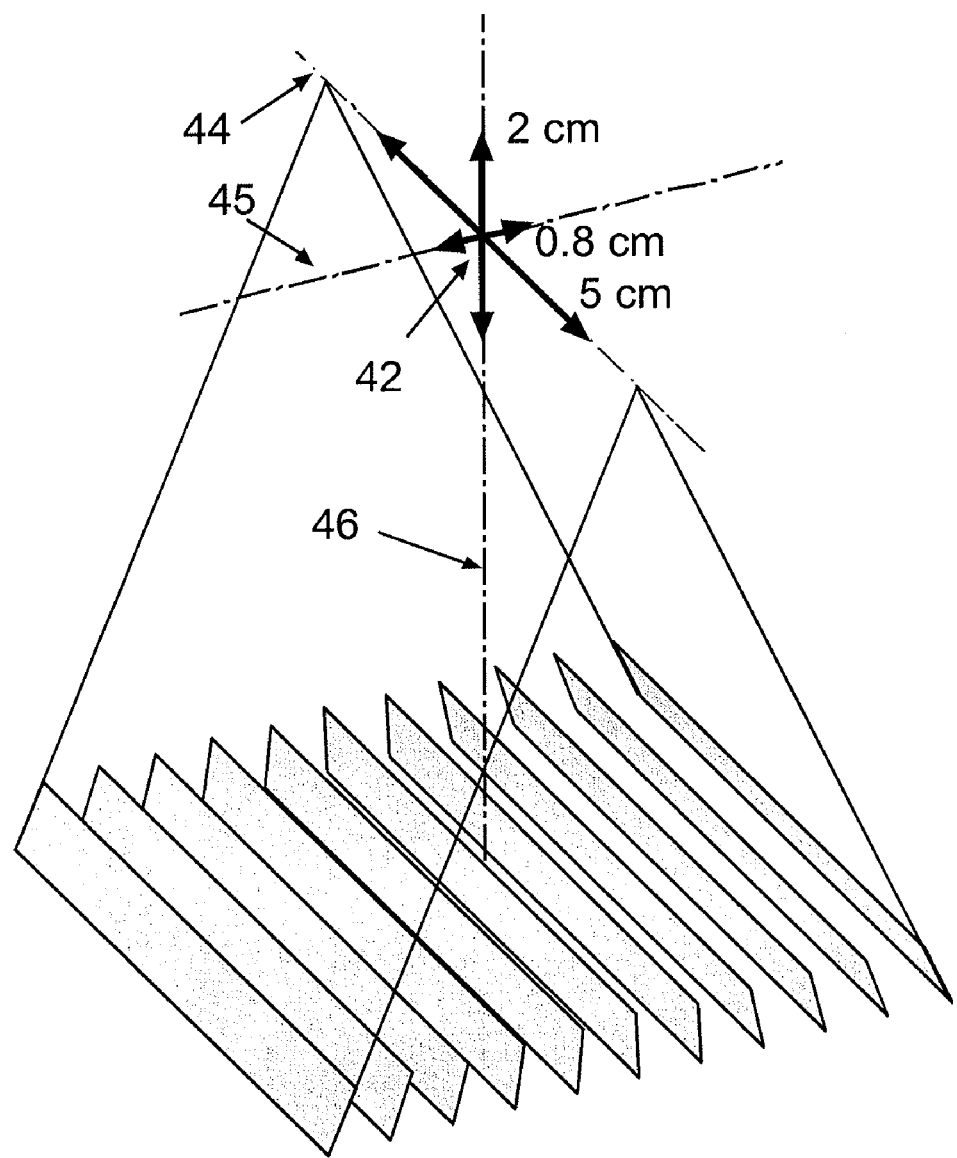
FIG. 4 is an illustration of the optimal and acceptable state of alignment for the mobile radiographic system of the present disclosure.

The processor analyzes images of the target array 28 acquired by the detector to determine the position and orientation of the target array 28 (which is equivalent to the position and orientation of the anti-scatter grid 32 in the grid tunnel 30) relative to a position on the mobile radiographic system 10. The processor then calculates the optimal position and orientation of the x-ray tube housing 22 such that the focal spot and/or central ray are in a state of alignment with regard to the anti-scatter grid 32 (FIG. 4). The motion control system directs the components of the mobile radiographic system 10 into a state of alignment.

The motion control system is manually operated by the operator with the aid of the processor and the directing element, which may alert the operator when at least one of the degrees of freedom of the mobile radiographic system is in the proper position. For example, the directing element may be a visual display which alerts the operator when the components are in the proper position. The processor may also lock any one of the degrees of freedom when it has the desired value. In another alternate embodiment, the motion control system is partially manually operated with the aid of the processor and directing element and is partially manually operated without the aid of the processor and directing element. In yet another alternate embodiment, one or more of the degrees of freedom is manually operated with the aid of the processor and directing element, and one or more of the degrees of freedom is automatically operated by the processor and an automatic drive system, such as a stepper or linear motor.

Referring to FIG. 4, the optimal location 42 of the focal spot is the intersection of the focal line 44 of the anti-scatter grid 32 and a line 46 normal to the surface of the anti-scatter grid 32 that passes through the center of the anti-scatter grid 32. This location is defined as the optimal focal spot position, and when the focal spot is in this location the transmission of x-rays through the anti-scatter grid 32 is at its maximum value. The x-ray source assembly is in its optimal orientation when the central ray of the x-ray beam passes through the center of the anti-scatter grid 32, and the long and short axes of the x-ray beam are parallel to the long and short axes of the grid tunnel 30. When the x-ray focal spot is in the optimal focal spot position 42 and the x-ray source assembly is in its optimal orientation, then the mobile radiographic system 10 is defined to have optimal alignment. The degrees of freedom of the mobile radiographic system may be moved appropriately to place the x-ray source assembly into an optimal alignment.

The focal spot is in an acceptable position if the transmission of primary x-rays through the grid is at least 90% of its maximum value over the entire anti-scatter grid 32, and if the focal spot is within 5 cm of the optimal focal spot position 42 in a direction parallel to the focal line 44. For example, for a standard size 12:1 anti-scatter grid 32 with a focal length of 100 centimeters, the focal spot position will be acceptable if it is on the focal line 44 and within 5 centimeters from the optimal focal spot position 42, on the normal line 46 and within 2 centimeters from the optimal focal spot position 42, or on a line 45 normal to both grid focal line 44 and the grid normal line 46 and within 0.8 centimeters of the optimal focal spot position 42. Similarly, the x-ray source assembly is in an acceptable orientation if the central ray of the collimated x-ray beam passes substantially close to the center of the grid, and the long and short axes of the collimated x-ray beam are substantially parallel to the long and short axes of the grid tunnel 30. When the x-ray focal spot is an acceptable position, and the x-ray source assembly is in an acceptable orientation, the system is defined to have acceptable alignment. The degrees of freedom of the mobile radiographic system may be moved appropriately to place the x-ray source assembly into an acceptable alignment.

While the detector 26 is illustrated affixed to the collimator housing 24, it is appreciated that the detector according to the present disclosure can be mounted in a variety of positions on a mobile radiographic system 10. It is further recognized that other detectors in addition to an optical detector, such as a camera, are operative herein. Such alternate detectors may be optical in nature, or be based on other principles such as magnetic interactions or ultrasound. Some of these detectors mat not require the target array 28, but may directly detect the grid tunnel 30 or target array 28, or fiducial markers attached directly to the grid tunnel 30 or target array 28.

In operation according to the present disclosure, grid tunnel 30, containing the anti-scatter grid 28 and the image receptor 34, is placed under an object to be radiographically imaged 1, such as a hospital patient. A radiological technician thereafter attaches the target arm 36 to the grid tunnel 30. The arm 36 fits into a channel 40 on grid tunnel 30 and extends past the lateral dimensions of the object 1. Thus, the end of the arm 36 is visible to the detector 26. The operator places the detector 26 in rough alignment with the target array 28. The rough alignment process may be aided by the use of a positioning element on the detector 26, such as the light source 25. After the rough alignment, a measuring protocol is activated by the operator. The detector 26 collects an image of the target array 28 and its fiducial markers 50 and transmits the data comprising the image to the processor. The processor calculates the position and orientation of the target array 28 and associated grid tunnel 30 using the fiducial markers 50, and therefore the anti-scatter grid 32, relative to the detector 26. Once the processor calculates the relative position and orientation information, the operator activates the motion control system. On activation of the motion control system, the processor and the directing element then direct the operator to move the system to a state of alignment as determined by the processor. The detector may collect a confirmatory image of the target array 28 to assure proper alignment of the mobile radiographic system.

The visual display 60 may alert the operator of the condition of the system 10 in addition to providing information regarding the current and/or desired position of the components of the mobile radiography system. For instance, the visual display 60 could indicate the detector 26 is unable to "see" all the fiducial markers 50 of the target array 28, or the detector "sees" all the fiducial markers 50, but is not yet aligned or that the system is ready for use. Other information may also be displayed. This status information could also be displayed in other ways, for instance with a series of LED lights. In addition, the mobile radiographic system 10 may have at least one control element, such as a button, toggle switch or similar device. The control elements may serve various functions as desired. For example, one control element may release the motion control system and allow the operator to roughly align the tube housing 22 with the target array 28. Another control element may activate the motion control system for alignment.

Figure 7:
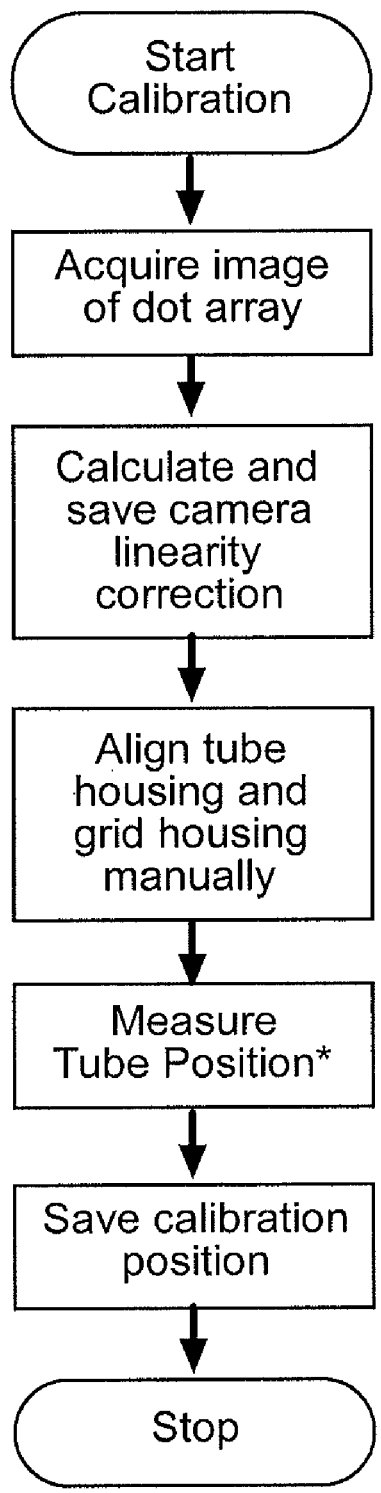
FIG. 7 is a flowchart illustrating the steps involved in the calibration procedure.
Figure 8:
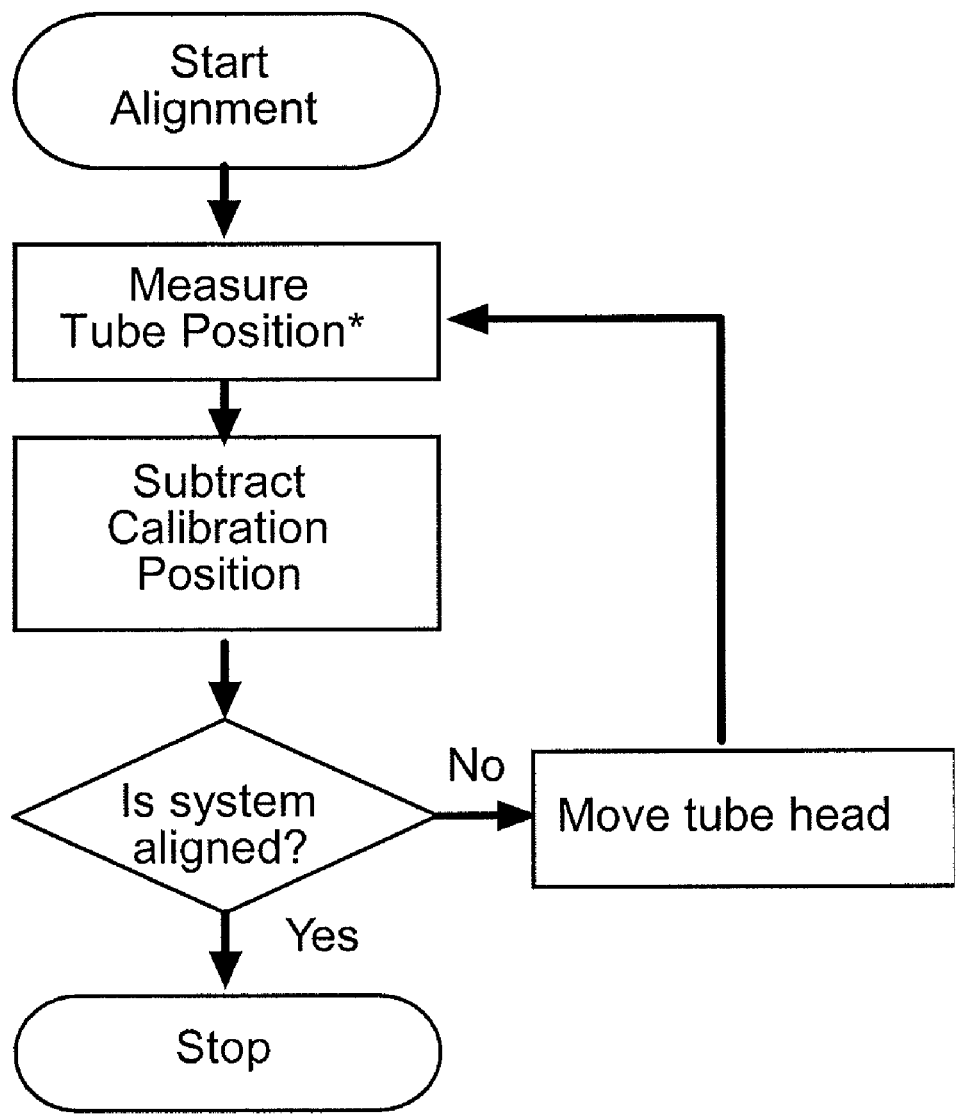
FIG. 8 is a flowchart illustrating the steps involved in the alignment procedure.

Before the system is used clinically, the mobile radiographic system 10 undergoes calibration. This calibration step needs be performed just once for a given mobile radiographic system 10 and target array 28, as the calibration information is stored in a calibration file. The first step in the calibration is to generate a correction for the spatial non-linearity of the detector 26. This is accomplished by acquiring an image of a matrix of black dots, and fitting the measured position of the dots to a mathematical function. Next, the detector 26 is mounted on the collimator 24, the target array 28 is mounted on the grid tunnel 30, and the tube housing 22 is positioned optimally so the x-ray focal spot falls on the focal line of the anti-scatter grid 32 as described herein (an optimal state of alignment). The techniques involved in centering the focal spot are common the field and are within the ordinary skill of one in the art. An image of the target array 28 is acquired and the processor then measures the position and orientation of the fiducial markers 50 on the target array 28 relative to the detector. The position of the tube housing is then determined. The results of this measurement are stored in the processor. The process is depicted diagrammatically in FIG. 7.

The first step in the clinical alignment procedure is to determine the position and orientation of the anti-scatter grid 32 relative to the tube housing 22 through the measurement of the position and orientation of the fiducial markers 50 on the target array 28. The detector 26 acquires an image of the target array 28 and transmits the data to the processor as described herein. The processor also receives data from the positional encoders in the components of the mobile radiographic system, which allows the processor to know the position of said components. The processor takes this data and calculates the position of the tube housing 22 relative to the console 14 so that the tube housing 22 will be in a state of alignment relative to the grid tunnel 30 and the anti-scatter grid 32, that is, the relative position stored during the calibration of the tube housing 22 (described above). The processor then provides this information to the display. The display then directs the operator regarding the movement of the tube housing 22 to the position determined by the processor so that the focal spot is in a state of alignment with the anti-scatter grid 32. In summary, the processor determines the position and orientation of the fiducial markers 50 of the target array 28 in relation to the x-ray tube housing 22, and uses this information to calculate a state of alignment for the mobile radiographic system 10, and the display, directed by the processor, directs an operator in the movement of the component of the mobile radiographic system to a state of alignment.

The x-ray source assembly has six degrees of freedom. Three degrees of freedom allow the x-ray source assembly to move to the central position on the focal line of the anti-scatter grid 32 (R, H, and $\Phi$), two degrees of freedom allow the x-ray source assembly to direct the central ray of the x-ray beam to the center of the anti-scatter grid 32 ($\Theta$ and $\Psi$) and one degree of freedom allows the collimator 24 to align with the long axis of the image receptor ($\Omega$) (discussed in more detail below). The processor measures the six Cartesian coordinates of the target array 28 in relation to the detector 26. Encoders in the mobile radiographic system measure the values of the six degrees of freedom and convey this information to the processor, which thereby determines the Cartesian coordinates of the detector 26 relative to the console 14. The processor compares the two sets of Cartesian coordinates and determines the six Cartesian coordinates of the target array 28 in relation to the console 14. The processor then determines the six Cartesian coordinates of the detector when the tube housing 22 is optimally aligned with the anti-scatter grid. Finally, the processor determines the values of the six degrees of freedom when the tube housing 22 is in a state of alignment.

It is appreciated that an acceptable degree of alignment can be accomplished with fewer than six degrees of freedom. For example, with three degrees of freedom (R, H, and $\Phi$), the focal spot could be placed at the center point on the focal line of the grid, aligning the focal spot with the grid. The operator could then manually adjust the remaining degrees of freedom without the aid of the processor and visual display. Generally, the collimator orientation ($\Omega$) and the source assembly rotation adjustments ($\Theta$ and $\Psi$) are generally small and less critical and can be done without the aid of the processor and display if desired. In principle, the focal spot could be moved onto the focal line with as few as two degrees of freedom, although with no guarantee that it would fall close to the line normal to the center of the grid. Such approaches align the source assembly and grid at the expense of more effort on the part of the user. Therefore, while the foregoing has described all six degrees of freedom being associated with a positional encoder in communication with the processor, the foregoing does not require that each of the six degrees of freedom have an associated positional encoder. For example, in one embodiment only three degrees of freedom may have an associated positional encoder, such as for example, R, H, and $\Phi$. In this embodiment, only those components associated with the three degrees of freedom would be displayed by the processor on the display.

Figure 9:
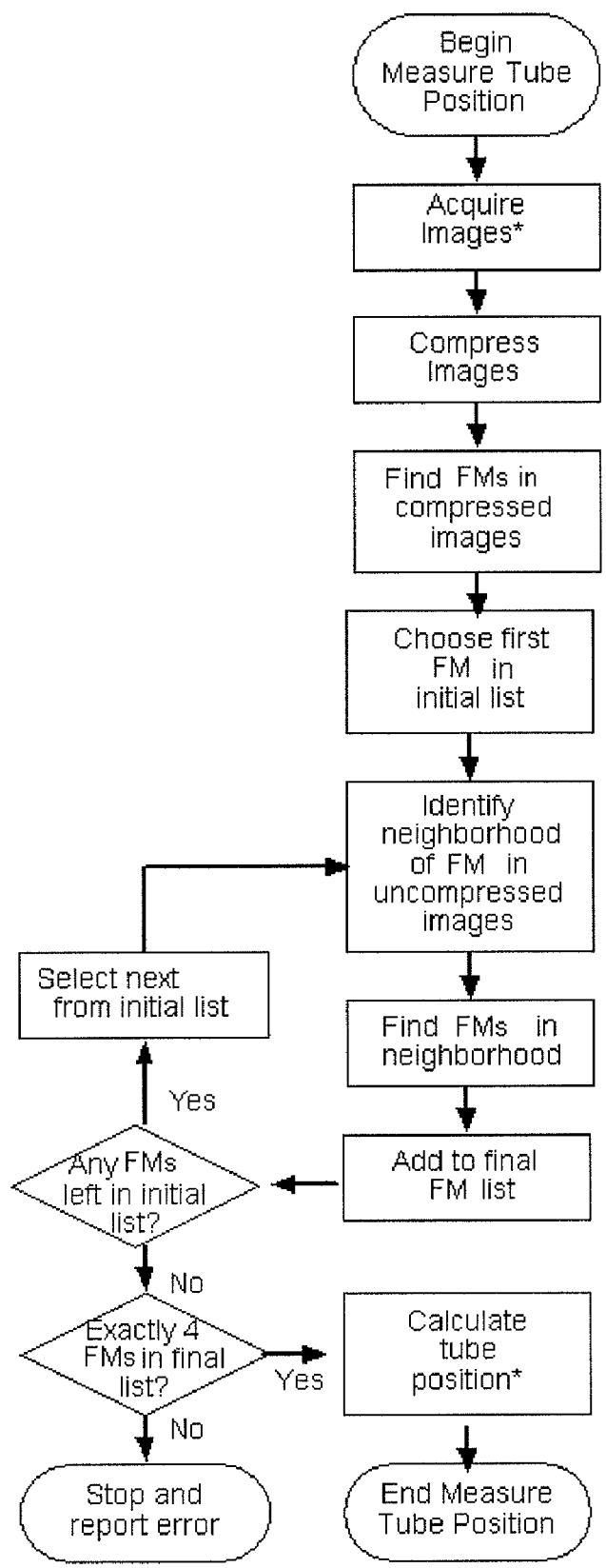
FIG. 9 is a flowchart illustrating the steps involved in measuring the position of the x-ray source assembly.
Figure 10:
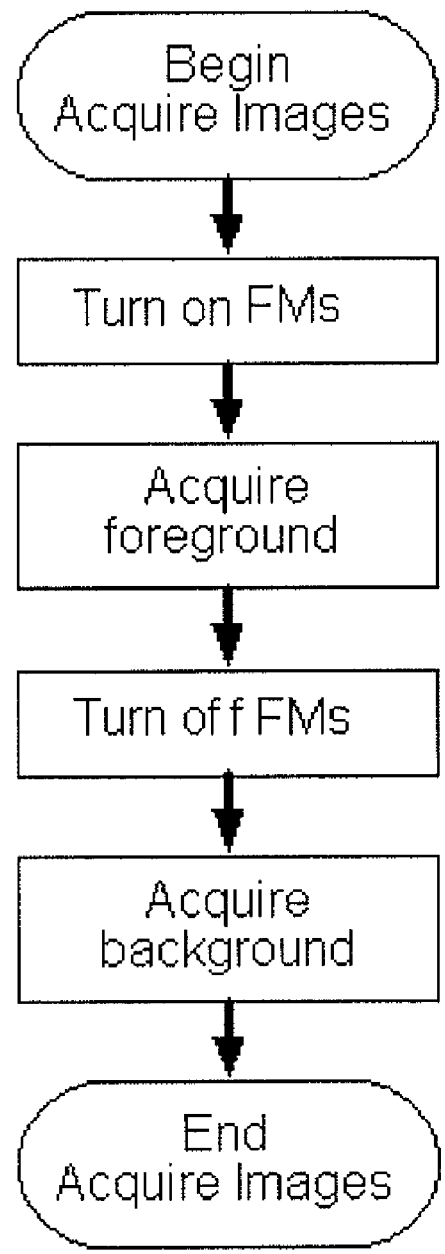
FIG. 10 is a flowchart illustrating the steps involved in acquiring an image of the target array.

FIG. 9 diagrammatically illustrates one embodiment of the steps involved in measuring the position of the tube housing 22. FIG. 10 shows an example of the image acquisition process. An image is acquired from the detector 26. The process may be varied depending on the nature of the fiducial markers 50. When the fiducial markers are light reflective substances, the detector acquires a first image (referred to as foreground) of the target array 28 with a light source 25 shining on the target array 28 (the light source may be mounted on the detector 26 or other components of the mobile radiographic system 10) and acquires a second image (referred to as background) with no light source shining on the target array 28. The processor subtracts the background image from the foreground image to produce an image that consists entirely of the light reflected back by the light reflecting material comprising the fiducial markers 50. This process increases the contrast of the fiducial markers relative to the background substantially. Alternately, only a single image may be acquired with the light source turned on and the fiducial markers located by the increase in intensity created by the light reflecting material. However, it is possible for any bright objects in the background to confuse the processor in this technique.

Figure 11:
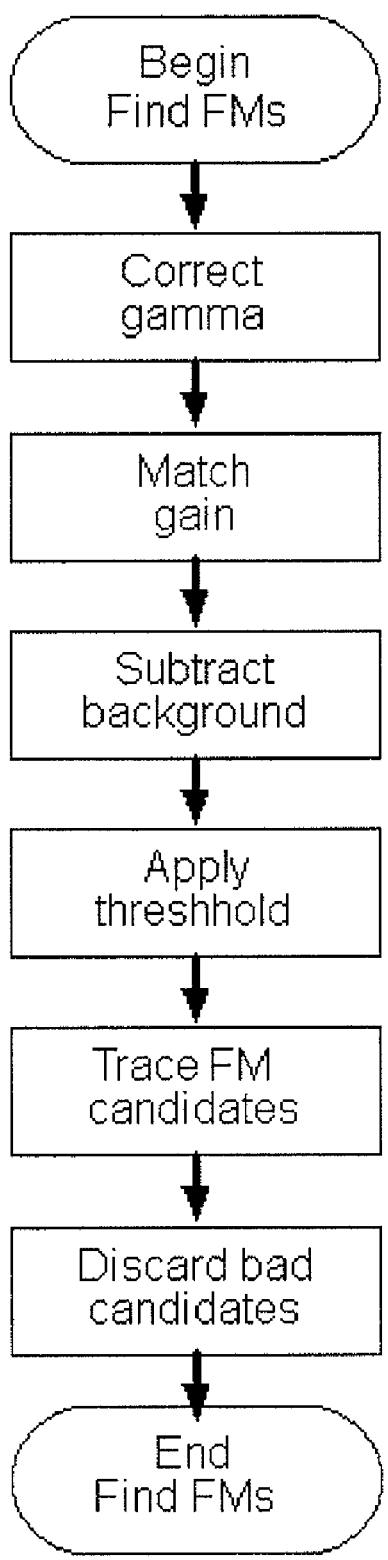
FIG. 11 is a flowchart illustrating the steps involved in the procedure of localizing individual fiducial markers on the target array.

The images acquired show the fiducial markers as areas of greater intensity as compared to the background. The acquired image is compressed in order to more efficiently locate the fiducial markers. The fiducial markers are then located in the compressed image, and the neighborhood (i.e., general area) of the fiducial markers is identified. This neighborhood is scanned in the uncompressed image to identify the exact position of the fiducial markers. One embodiment of a sequence for locating fiducial markers is shown in FIG. 11. The images are gamma corrected so that the pixel values are proportional to the intensity of the fiducial markers. The gains of the first and second images are then matched. The background image is then subtracted from the foreground image. A threshold is then applied to the difference image and pixels with intensities above the thresholds are marked as possible candidates for the location of a fiducial marker. The fiducial marker candidates are traced and analyzed, and candidates that do not meet certain criteria (for example, size, shape, color, intensity, etc.) are discarded. Finally, a list of candidate fiducial marker positions is returned to the calling process.

By locating the general position of the fiducial markers in a compressed image, the speed of the process is greatly increased. Any fiducial markers in the neighborhood are identified and added to a final list of fiducial marker locations. The identification steps are repeated until all fiducial markers are located and added to the final list of fiducial markers locations. If the final list does not contain exactly the required number of fiducial markers, the measurement process is terminated and an error light may be displayed. If the correct number of fiducial markers is in the final list, the tube housing 22 position is calculated (as shown in FIGS. 9 and 11).

Figure 12:
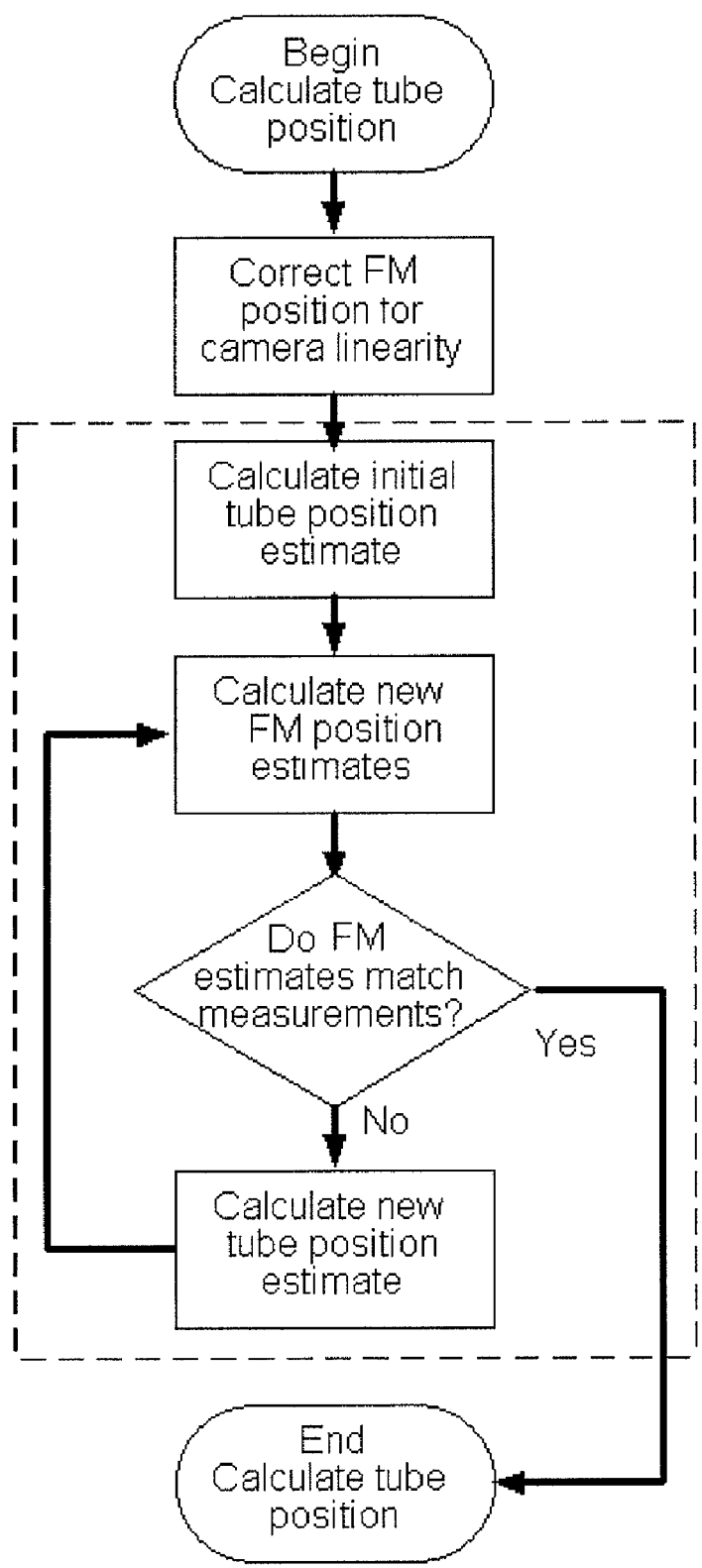
FIG. 12 is a flowchart illustrating the steps involved in the calculating the position of the x-ray source assembly.

FIGS. 9 and 12 describe how the fiducial marker information is analyzed to determine the position of the detector 26 relative to the target array 28, and by inference the position and orientation of the tube housing 22 relative to the anti-scatter grid 32. First, the detector linearity calibration is used to convert the centroid of each fiducial marker (in pixel units) to a physical position (in cm) projected onto a fiducial image plane. The Marquardt algorithm is used to calculate the position of the target array relative to the tube housing 22 from these measurements. The Marquardt algorithm is a general iterative algorithm for fitting a non-linear function to a set of data, starting from an initial estimate of the function parameters. The implementation generates the initial estimate by assuming that the distance to the detector is infinite, and that the magnification of the detector image is unknown. The iterations continue until a convergence criterion is reached. The final estimated parameters are considered good if the measured and estimated fiducial marker positions match to within some limit (e.g. 0.05 cm). The mathematics involved in the calculation of the algorithm to convert the position measurements of the fiducial markers to a desired position and orientation of the tube housing 22 involve Cartesian coordinate transformation. The details of this field of mathematics are well known to those of ordinary skill in the art. As noted above, the processor uses this information to determine the desired values of the various degrees of freedom of the system.

In response to calculation of the position and orientation information, the processor provides this information to the directing element, such as a visual display, which directs an operator to adjust at least one degree of freedom to move the x-ray tube housing to a state of alignment with the anti-scatter grid.

In one embodiment the x-ray tube housing 22 has six degrees of freedom, as discussed above. Three degrees of freedom correspond to the three spatial dimensions of the focal spot location (R, H, and $\Phi$), two degrees of freedom correspond to the direction (altitude and azimuth) of the central ray of the X-ray beam ($\Theta$ and $\Psi$), and one degree of freedom corresponds to a rotation of the collimator around the X-ray beam ($\Omega$). A portion of the motion control system as well as a positional encoder may be associated with each degree of freedom to direct this motion under the direction of the processor. However, as discussed above, fewer than all six degrees of freedom may be associated with a positional encoder.

In one embodiment (FIG. 13), the X-ray tube housing 22 is mounted in a gimbal 23. The gimbal 23 is mounted on a horizontal extensible arm 20, which in turn is mounted to a vertical column 16. The X-ray collimator housing 24 is movably mounted on the x-ray tube housing 22. Each of these degrees of freedom will be described briefly and are illustrated in FIG. 13. The arm 20 can be extended or retracted (motion R), the column 16 can be moved up and down (motion H), and the column can be rotated about a vertical axis (motion $\Phi$). The three motions R, H, and $\Phi$ together provide the three degrees of freedom necessary to locate the center of the x-ray tube housing 22 on gimbal 23 at a desired spatial location.

Once the x-ray tube housing 22 on gimbal 23 is located at a desired location, the two bearings of the gimbal can be rotated (motions $\Theta$ and $\Psi$) defining two additional directional degrees of freedom. If the focal spot is located at the intersection of the axes of motions $\Theta$ and $\Psi$, then its position is determined uniquely by motions H, R, and $\Phi$. Otherwise, the position of the focal spot is determined also by motions $\Theta$ and $\Psi$ as well. The last degree of freedom lies in the rotation $\Omega$ of the collimator housing 24 around the central ray of the X-ray beam.

The processor directs the operator regarding the direction and amount of movement of at least one freedom of movement H, $\Phi$, R, $\Theta$, $\Psi$ and $\Omega$, to place the x-ray tube housing in a state of alignment. The information is provided to the operator by the directing element, such as visual display 60. These movements could be accomplished by the operator sequentially or in parallel. Parallel movement might have the advantage of reduced alignment time, but the disadvantage of increased complexity and possible distraction of the technologist by a relatively complex motion. In one embodiment, the processor provides the operator with the direction and amount of movement in the degree of freedom H, $\Phi$ and R to place the gimbal in its desired location. Once the gimbal is in its desired location, the processor provides the operator with the direction and amount of movement for the three remaining freedoms of motion, $\Theta$, $\Psi$ and $\Omega$, to orient the x-ray beam and collimator to a state of alignment. As stated above, the processor need not provide direction and amount of movement information for each degree of freedom incorporated in the mobile radiographic system.

As discussed herein, the movement directed by the processor is manual movement, requiring the operator to physically move one or more degrees of freedom of the mobile radiography system.

In one embodiment, drive elements are associated with one or more of the degrees of freedom are manual drive elements, such as but not limited to gears, pulleys or other elements known in the art for accomplishing movement. It should be noted that the processor is not required to communicate information to the drive elements of the motion control system; the processor may simply provide, via the directing element, the direction and amount of movement required for a degree of freedom so as to direct the operator in the manual movement. In the embodiment illustrated, the directing element is a visual display 60 in communication with the processor. The display 60 provides the direction and amount of movement in one or more of said degrees of freedom to position the components of the mobile radiography system to their desired location (which may be a state of alignment). The operator uses this information to manually move the x-ray source assembly according to the information on the display. In one embodiment when the operator uses sequential movement, the display may show the required change in one degree of freedom in order to move the selected degree of freedom to a desired position. The operator manually adjusts this degree of freedom, with the display continuously updating the required movement, until the degree of freedom is in the desired location. At this point, the processor may optionally direct the motion control system to lock the degree of freedom in place or the operator may manually lock the degree of freedom in place. The display then shows the required change in the next degree of freedom in order to move the selected degree of freedom to a desired position. Again, operator manually adjusts this degree of freedom, with the display continuously updating the required movement, until the degree of freedom is in the desired location. The processor may again lock the degree of freedom in place or the operator may manually lock the degree of freedom in place. The process is repeated for the remaining degrees of freedom until all the degrees of freedom of the mobile radiography system are in the desired location. In one embodiment, the display shows the desired movement for at least one degree of freedom. In an alternate embodiment, the display shows the desired movement for two or more degrees of freedom. In yet another embodiment, the display shows the desired movement for all degrees of freedom.

In an alternate embodiment when the operator uses parallel movement, the display may show the required change in more than one degree of freedom in order to move the selected freedoms of motion to a desired position. The operator manually adjusts these degrees of freedom, with the display continuously updating the required movement, until the freedoms of motion are in the desired location. When one or more freedoms of motion are in the desired location, the processor may optionally direct the motion control system to lock theses freedoms of motion in place or the operator may manually lock these freedoms of motion in place. Any degree of freedom that is not yet in a desired position will remain unlocked until the desired position is achieved.

In yet another embodiment, the operator may manually move at least one degree of freedom as directed by the directing element under the control of the processor as described herein and at least one degree of freedom may be automatically moved by the motion control system as described in U.S. Pat. No. 6,702,459. In this embodiment, a manual motion control system and an automatic motion control system are present in the mobile radiography system. The automatic motion control system comprising an automatic drive element, such as but not limited to a servo motor, for at least one of said degree of freedom in communication with said processor. The processor thereby directs the movement of said at least one degree of freedom without operator involvement.

Optionally, the operating console 14 is equipped with an inner lock disabling the x-ray exposure until the x-ray focal spot and grid have been aligned according to the present disclosure. Further, it is appreciated that an increase in tube voltage is expected to provide improved images as compared to imaging done absent an anti-scatter grid. The increase in tube voltage is intended to increase x-ray transmission through the patient 1 and thereby allow a shorter exposure time. Optionally, a mobile radiographic system according to the present disclosure is provided with an alarm system which is activated upon movement of the mobile radiographic system 10 absent grid tunnel 30 to prevent accidental loss of the grid tunnel 30 and the target arm 28.

It is appreciated that localization techniques can be performed not only by the optical methods detailed herein, but also through the use of magnetic dipole technology and/or ultrasound technology. Magnetic dipole arrays and sensors operating with the benefit of current loops or electromagnets are detailed in U.S. Pat. No. 4,054,881.

Patents and publications mentioned in this specification are indicative of the levels of those skilled in the art to which the disclosure pertains. These patents and publications are incorporated herein by reference to the same extent as if each individual patent or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

REFERENCES

1. Barnes G T: Contrast and Scatter in X-Ray Imaging. *RadioGraphics* 11:307-323, 1991.
2. Niklason L T, Sorenson J A, Nelson J A: Scattered Radiation in Chest Radiography. *Med. Phys.* 8:677-681, 1981.
3. Tucker D M, Souto M, Barnes G T: Scatter in Computed Radiology. *Radiology* 188:271-274, 1993.
4. Niklason L T, Barnes G T, Carson P: Accurate Alignment Device for Portable Radiography. *Radiology* 173(P):452, 1989.
5. O'Donovan P B, Skipper G J, Litchney J C, Salupo A J, Bortnick J R: Device for Facilitating Precise Alignment in Bedside Radiography. *Radiology* 184:284-285, 1992.
6. Press W H, Flannery B P, Teukolsky S A, Vetterling W T, Numerical Recipes in C: The Art of Scientific Computing, Cambridge University Press, Cambridge UK, 1988.

What is claimed:

1. A mobile radiographic system, the system comprising:
  a. an x-ray source assembly, said x-ray source assembly comprising an x-ray tube housing having an x-ray source with a focal spot, a tube housing mounting adjustably supporting said x-ray tube housing, said x-ray tube housing adjustably mounted to an adjustable support and an x-ray collimator adjustably coupled to the x-ray tube housing, said x-ray source assembly being adjustable with regard to at least one degree of freedom allowing the x-ray tube housing to be moved to a desired location and orientation with respect to an anti-scatter grid;
  b. said anti-scatter grid not being in a fixed position and orientation relative to the x-ray tube housing;
  c. a measuring system, said measuring system comprising a positional encoder for at least one of said degrees of freedom and a detector for acquiring position and orientation information of the anti-scatter grid relative to a fixed point on the mobile radiographic system;
  d. a manual motion control system to direct the movement of at least three of said degrees of freedom, said motion control system comprising a drive element for at least one of said degrees of freedom and a directing element;
  e. a processor in communication with said detector, said encoder and said directing element, the processor determining the desired value of the at least one degree of freedom so that the x-ray tube housing will be in a state of alignment, the processor not being in communication with the drive element, wherein an operator sequentially adjusts groups of degrees of freedom, adjusting in parallel the degrees of freedom within each group, where each degree of freedom is manually adjusted by the operator as directed by the directing element.

2. The system of claim 1 where each said degree of freedom is locked in place by the processor or the operator once said desired value is achieved.

3. The system of claim 1 where at least one of the group of degrees of freedom comprise a single degree of freedom, and at least one of the degrees of freedom is not locked in place by the processor or the operator once said desired value is achieved.

4. The system of claim 1 where the directing element provides the current location, the desired location of said at least one degree of freedom.

5. The system of claim 1 where said directing element provides a direction and an amount of movement of said at least one degree of freedom to adjust said at least one degree of freedom to said desired value.

6. The method of claim 1 where the directing element is visual in nature, tactile in nature or auditory in nature.

7. The method of claim 6 where the directing element is a visual display.

8. The system of claim 1 where said at least three degrees of freedom are H, R and Φ.

9. The system of claim 8 where said at least three degrees of freedom are locked in place by the processor or the operator once said desired values are achieved.

10. The system of claim 1 where said measuring system comprises a positional encoder for each of said six of said degrees of freedom.

11. The system of claim 10 where an operator moves said six degrees of freedom as instructed by the directing element to adjust said six degrees of freedom to said desired values.

12. The system of claim 10 where said six degrees of freedom are locked in place by the processor or the operator once said desired values are achieved.

13. The system of claim 1 where the detecting element comprises a target array having a plurality of fiducial markers in a fixed position relative to the anti-scatter grid, and a detector acquiring position and orientation information of the target array relative to the mobile radiographic system.

14. The system of claim 13 where the detector is mounted on the collimator or on the x-ray tube housing.

15. The system of claim 13 where the fiducial markers are light reflecting targets, magnetic targets, sound emitting targets, variously colored light emitting diodes or monochrome light emitting diodes.

16. The system of claim 13 where the fiducial markers are light reflecting targets and the system further comprises a light source to illuminate said light reflecting targets.

17. The system of claim 16 where said light reflecting targets are manufactured from a retro-reflective material.

18. The system of claim 13 where said fiducial markers are separated by a known distance.

19. The system of claim 13 where said fiducial markers are not located in one plane.

20. The system of claim 13 where the detector is an optical detector, a magnetic detector or an ultrasound detector.

21. The system of claim 20 where the optical detector is a still frame digital camera, a digital video camera or an analog video camera.

22. The system of claim 1 where said desired location and orientation is a state of alignment.

23. The system of claim 22 where said state of alignment is an optimal state of alignment or an acceptable state of alignment.

24. The system of claim 1 where the anti-scatter grid is contained within a grid tunnel.

* * * * *